(12) United States Patent
Rodriguez et al.

(10) Patent No.: US 10,213,577 B2
(45) Date of Patent: Feb. 26, 2019

(54) METHODS FOR ENHANCING EXPOSURE THERAPY USING PAIRING WITH VAGUS NERVE STIMULATION

(71) Applicants: MicroTransponder, Inc., Austin, TX (US); The Board of Regents, The University of Texas System, Austin, TX (US)

(72) Inventors: Christa Mcintyre Rodriguez, Richardson, TX (US); Navzer Dara Engineer, Plano, TX (US); Michael P. Kilgard, Richardson, TX (US)

(73) Assignees: MICROTRANSPONDER, INC., Austin, TX (US); THE BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/808,509

(22) Filed: Jul. 24, 2015

(65) Prior Publication Data
US 2015/0328458 A1     Nov. 19, 2015

Related U.S. Application Data

(60) Continuation-in-part of application No. 12/485,040, filed on Jun. 15, 2009, now Pat. No. 9,089,707, and
(Continued)

(51) Int. Cl.
*A61N 1/00* (2006.01)
*A61M 21/00* (2006.01)
(Continued)

(52) U.S. Cl.
CPC ............ *A61M 21/00* (2013.01); *A61N 1/361* (2013.01); *A61N 1/36014* (2013.01);
(Continued)

(58) Field of Classification Search
CPC ............ A61N 1/36053; A61N 1/36092; A61N 1/36089; A61N 1/36096; A61N 1/36103; A61N 1/361
See application file for complete search history.

(56) References Cited

U.S. PATENT DOCUMENTS

| 4,867,164 A | 9/1989 | Zabara |
| 5,299,569 A | 4/1994 | Wernicke et al. |

(Continued)

OTHER PUBLICATIONS

George, Mark S., et al. "A pilot study of vagus nerve stimulation (VNS) for treatment-resistant anxiety disorders." Brain stimulation 1.2 (2008): 112-121.*

(Continued)

*Primary Examiner* — Mallika D Fairchild
(74) *Attorney, Agent, or Firm* — Hauptman Ham, LLP

(57) ABSTRACT

Disclosed is a method of enhancing exposure therapy comprising providing an exposure therapy to a patient and stimulating the patient's vagus nerve at the same time as the exposure therapy. Also disclosed is a post-traumatic stress disorder therapy method comprising providing an exposure event to a patient and stimulating the patient's vagus nerve during the exposure event. Also disclosed is a phobia disorder therapy method comprising providing an extinction event to a patient and stimulating the patient's vagus nerve during the exposure event. Also disclosed is an obsessive compulsive disorder therapy method comprising providing a therapy event to a patient and stimulating the patient's vagus nerve during the therapy event. Also disclosed is an addiction disorder therapy method comprising providing a therapy event to a patient and stimulating the patient's vagus nerve during the therapy event.

30 Claims, 3 Drawing Sheets

Related U.S. Application Data a division of application No. 13/095,570, filed on Apr. 27, 2011, now Pat. No. 9,089,703.

(60) Provisional application No. 61/077,648, filed on Jul. 2, 2008, provisional application No. 61/078,954, filed on Jul. 8, 2008, provisional application No. 61/086,116, filed on Aug. 4, 2008, provisional application No. 61/149,387, filed on Feb. 3, 2009.

(51) Int. Cl.
*G09B 23/28* (2006.01)
*A61N 1/36* (2006.01)
*A61M 21/02* (2006.01)

(52) U.S. Cl.
CPC ..... *A61N 1/36017* (2013.01); *A61N 1/36025* (2013.01); *A61N 1/36053* (2013.01); *A61N 1/36092* (2013.01); *A61N 1/36096* (2013.01); *A61N 1/36103* (2013.01); *G09B 23/28* (2013.01); *A61M 21/02* (2013.01); *A61M 2021/0027* (2013.01); *A61M 2021/0044* (2013.01); *A61M 2021/0072* (2013.01); *A61N 1/36082* (2013.01); *A61N 1/36089* (2013.01)

(56) References Cited

U.S. PATENT DOCUMENTS

| | | |
|---|---|---|
| 5,578,061 A | 11/1996 | Stroetmann et al. |
| 6,104,956 A | 8/2000 | Naritoku et al. |
| 6,425,764 B1 | 7/2002 | Lamson |
| 7,076,307 B2 | 7/2006 | Boveja et al. |
| 2007/0027500 A1 | 2/2007 | Maschino et al. |
| 2007/0179534 A1 | 8/2007 | Firlik et al. |

OTHER PUBLICATIONS

Of Palyo et al (Palyo, Sarah, A., et al. "Post-traumatic stress disorder symptoms, pain and perceived life control: associations with psychosocial and physical functioning." Pain. Sep. 2005 117(1-2), 121-127.*

\* cited by examiner

METHODS FOR ENHANCING EXPOSURE THERAPY USING PAIRING WITH VAGUS NERVE STIMULATION

CROSS-REFERENCE TO RELATED APPLICATIONS

This application is a Divisional of U.S. patent application Ser. No. 13/095,570, filed on Apr. 27, 2011, which claims the benefit of U.S. Provisional Patent Application No. 61/328,621, filed Apr. 27, 2011. U.S. patent application Ser. No. 13/095,570 is also a Continuation-In-Part of U.S. patent application Ser. No. 12/485,040, filed Jun. 15, 2009, which claims the benefit of: U.S. Provisional Patent Application No. 61/077,648, filed Jul. 2, 2008; U.S. Provisional Patent Application No. 61/078,954, filed Jul. 8, 2008; U.S. Provisional Patent Application No. 61/086,116, filed Aug. 4, 2008; and U.S. Provisional Patent Application No. 61/149,387, filed Feb. 3, 2009. All of these applications are incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Exposure therapy is a recognized treatment for anxiety disorders such as phobia, post-traumatic stress disorder (PTSD), obsessive-compulsive disorder, and relapse of drug abuse. Adjunct treatment with memory enhancing drugs has been shown to enhance the efficacy of exposure therapy in the treatment of phobia disorder. Vagus Nerve Stimulation (VNS) has been shown to enhance the consolidation of new memories, likely through modulation of brain plasticity. VNS paired precisely with a specific tone induces cortical plasticity and has been used to effectively treat tinnitus in rats. Clinical trials examining tinnitus treatment in humans are currently underway. Enhancement of exposure therapy would have obvious implications for the treatment of anxiety disorders.

SUMMARY

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

In an embodiment, the disclosure includes a method of enhancing exposure therapy comprising providing an exposure therapy to a patient and stimulating the patient's vagus nerve at the same time as the exposure therapy.

In an embodiment, the disclosure includes a post-traumatic stress disorder therapy method comprising providing an exposure event to a patient and stimulating the patient's vagus nerve during the exposure event.

In an embodiment, the disclosure includes a phobia disorder therapy method comprising providing an extinction event to a patient and stimulating the patient's vagus nerve during the exposure event.

In an embodiment, the disclosure includes an obsessive-compulsive disorder therapy method comprising providing a therapy event to a patient and stimulating the patient's vagus nerve during the therapy event.

In an embodiment, the disclosure includes an addiction disorder therapy method comprising providing a therapy event to a patient and stimulating the patient's vagus nerve during the therapy event.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
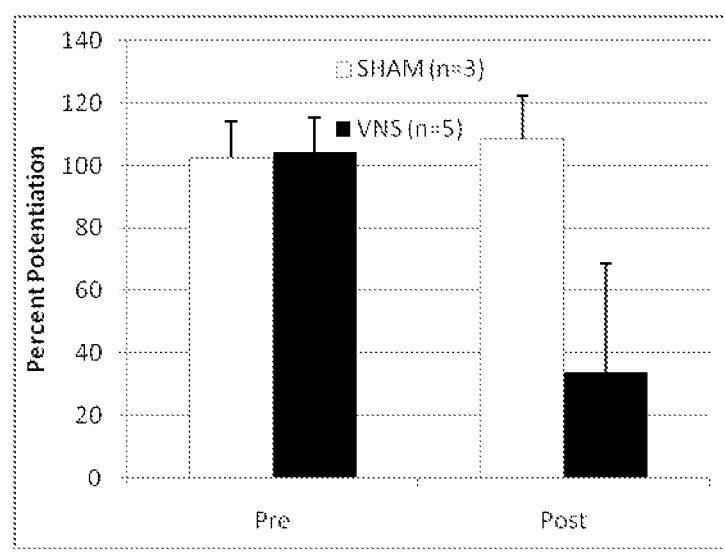
FIG. 1 is a graph showing VNS enhances extinction of fear-potentiated startle.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents. The present application describes several embodiments, and none of the statements below should be taken as limiting the claims generally.

Typically, conditioned fear associations are formed (consolidated), and then replaced with new associations (extinction). Problems manifest when conditioned fears form but are not naturally extinguished. Consolidation and extinction are related processes. Normal extinction processes depend on the consolidation of new memories. Vagus nerve stimulation has been shown to improve memory consolidation.

Memory disorders like PTSD can take months to develop following the initial exposure to the traumatic events and even longer for sufferers to seek treatment. Potential treatments should be effective when initiated long after a trauma. Extinction training may be performed two weeks after induction of the initial fear conditioning. Since the spontaneous recovery of fear memories after extinction has been observed in human and nonhuman animals, it was also examined whether the effects of VNS treatment are long lasting. For this purpose, animals were tested a second time, two weeks after extinction training.

VNS is approved by the Food and Drug Administration (FDA) for treatment of intractable epilepsy and depression. Beneficial effects of VNS such as enhanced cognition in patients with epilepsy and Alzheimer's disease have been reported. By combining vagal stimulation with Exposure Therapy, the natural extinction process that protects most people from developing PTSD may be facilitated. The brain may be rehabilitated by targeting the systems involved in the consolidation of the initial traumatic memory.

Because of the tight temporal and spatial control associated with brief VNS, this approach may target more efficiently the brain areas and synapses that support PTSD than using drug therapy. Since VNS is known to decrease the stress response of the sympathetic nervous system, it may increase the effectiveness of traditional talk therapy or emerging virtual reality therapies by reducing the possibility that patients will associate exposure therapy cues with anxiety.

The cause of PTSD remains unknown, but psychological and physical alterations have been identified in PTSD patients that suggest VNS therapy would be highly effective at helping these particular patients to extinguish traumatic associations. Several reports have identified evidence of an impaired ability to extinguish former associations in PTSD subjects. Long-term consolidation of emotionally arousing memories requires vagus nerve-initiated activation of the nucleus of the solitary tract.

Accordingly, it is likely that impaired vagal tone would adversely affect consolidation of extinction memory. Decreased vagal tone has been observed in human subjects with PTSD. Low basal cortisol levels, a disconnection in the normal modulation of the amygdala by the medial prefrontal cortex, increased sympathetic, and decreased parasympathetic tone have also been observed in PTSD patients.

Research findings demonstrate the potential for reversal of these PTSD-associated abnormalities with VNS treatment. VNS enhances memory consolidation, modulates cortisol levels, increases norepinephrine release in both the amygdala and medial prefrontal cortex, and alters the balance of sympathetic to parasympathetic activity in the autonomic nervous system.

The failure to naturally extinguish conditioned fears leads to PTSD and the goal of Exposure Therapy is to extinguish such memories. Fear conditioning and extinction are readily quantifiable in laboratory rats and extinction training is traditionally used as an animal model of Exposure Therapy. Thus, extinction training may be used in rats as a model for Exposure Therapy for conducting tests of feasibility. Further, tests of VNS-induced cognitive enhancement revealed that similar VNS parameters also occur in rats and human patients.

Using two different measures of fear conditioning, it was found that VNS pairing produces better and improved rapid extinction of fear responses. VNS pairing enhances extinction even when administered about two weeks after training, suggesting that even a relatively well-consolidated memory is responsive to the therapy. No evidence for spontaneous recovery of fear after about two weeks was found.

Experiments were designed to determine if paired VNS therapy could enhance the efficacy of extinction training in a rat model. It was evaluated whether paired VNS enhances extinction in rats that were recently trained on a fear-conditioning task. The efficacy of VNS when given about two weeks after the initial fear conditioning was also evaluated. This is relevant since most patients seek intervention after the conditioned fear fails to automatically extinguish over time. The sensitivity of VNS-enhanced extinction to relapse was evaluated since the benefits of traditional exposure therapy are often transient.

Results demonstrated both enhanced and accelerated extinction. Two different measures of fear conditioning were examined. A fear-potentiated startle task uses an accelerometer to measure the startle response as an indicator of fear conditioning. Rats conditioned to fear a light demonstrated greater startle responses to an abrupt burst of white noise in the presence of the light.

Both constant current and voltage controlled capacitive discharge stimulation were used to test auditory fear conditioning. Both were effective.

The results and findings indicate that exposure therapy can be enhanced by providing an exposure therapy to a patient while simultaneously stimulating the patient's vagus nerve. The nature of the exposure therapy may depend on the condition being treated. For example, for post-traumatic stress disorder, the therapy event may be a sensory recreation of the traumatic event, presented in a controlled environment.

The precise timing of the paired VNS pulse may depend on the nature of the therapy event. The results indicate that the paired VNS pulse may be given during the therapy rather than before or after, although some overlap is not contraindicated. Where a trigger event can be identified in the therapy event, such as a tone or flash, the pairing can be derived from the trigger event.

Exposure therapy of this kind can be used to treat post-traumatic stress disorder, phobic disorders, obsessive-compulsive disorder, addiction disorders including addiction relapse, and other memory extinction disorders. VNS can be paired effectively with any of these known therapies.

With reference to FIG. 1, a graph shows that after a single extinction session, rats that were given VNS paired with the conditioned stimulus (light) showed significantly lower startle responses than sham-treated controls. In the auditory fear-conditioning paradigm, freezing is the measure of fear conditioning. Conditioned rats freeze in the presence of a tone that was associated with a foot-shock during training.

Figure 2:
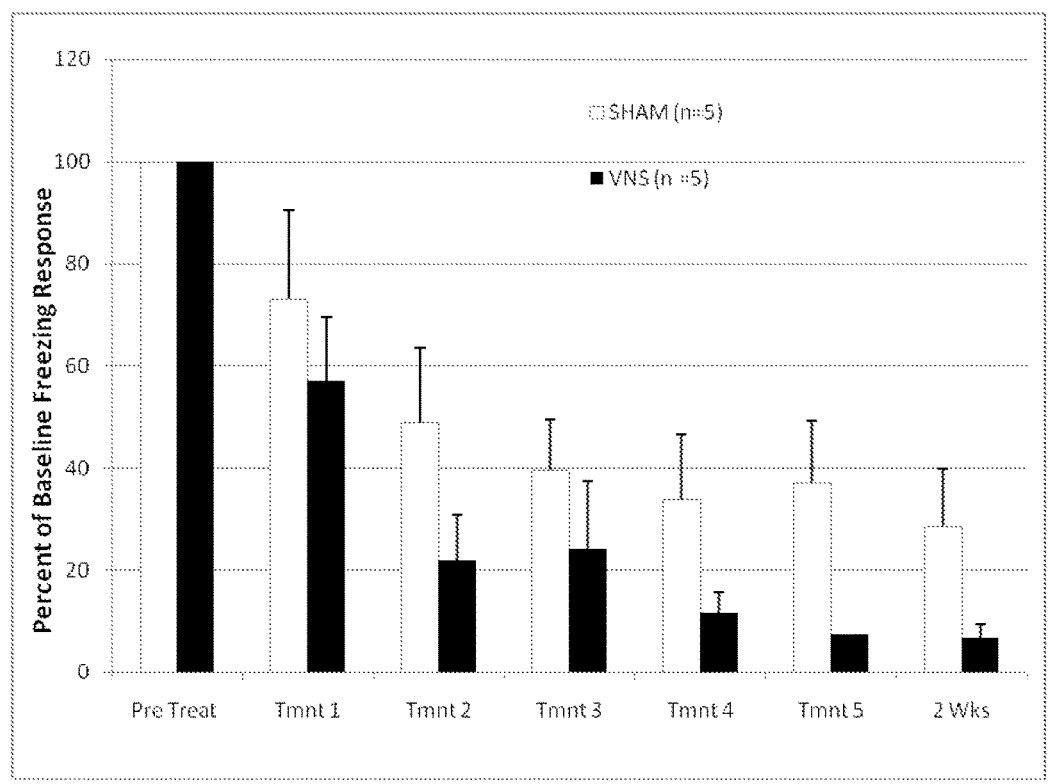
FIG. 2 is a graph showing VNS facilitates extinction of auditory fear conditioning.

With reference to FIG. 2, a graph shows that VNS-treated rats expressed less freezing after a single extinction session. Moreover, they achieved complete remission from freezing (freezing less than about 20% of the test time) after three sessions, whereas sham-treated controls did not reach full remission and seemed to plateau after three extinction sessions. These findings suggest that VNS pairing may enhance and accelerate the effects of exposure therapy.

VNS enhances extinction after a single session (FIG. 1) and accelerates remission of the fear response (FIG. 2). Fear potentiated startle scores were computed as [(startle amplitude on light-sound burst minus sound burst-alone trials)/sound burst-alone trials]×100. An analysis of variances (ANOVA) revealed a significant effect and Fisher's post hoc test revealed a significant treatment effect after a single trial (using Fisher's protected least significant difference (PLSD) $p=0.0221$ vs. sham control). Freezing scores (FIG. 2) were normalized to pre-VNS treatment values and a repeated measures ANOVA (Subject (Stimulation type)*treatment day) was used to assess differences over the treatment trials. Fisher's post hoc test was used to identify group differences. The effect of treatment day on freezing is significant $F((3, 24)=8.994, p<0.001)$. A post hoc analysis revealed a significant treatment effect of exponential stimulation on freezing relative to sham controls (Fisher's PLSD, $p=0.0356$). Spontaneous recovery of fear was not observed in either group at about two weeks after completion of extinction trials. The error bars are standard error of the mean (SEM).

VNS-facilitated extinction remained after about two weeks. Treated rats were significantly different from the control group at the two-week time point, suggesting that the effects of VNS were not transient.

Figure 3:
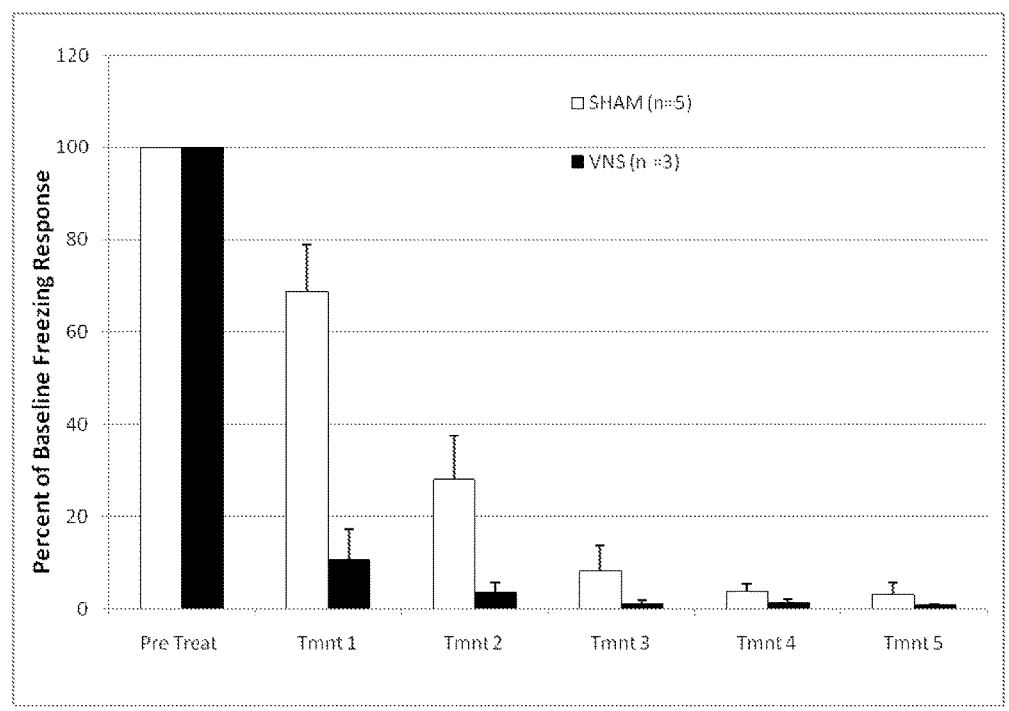
FIG. 3 is a graph showing VNS facilitates extinction when given two weeks after auditory fear conditioning.

With reference to FIG. 3, the graph depicts the freezing scores normalized to pre-VNS treatment values and a repeated measures ANOVA (Subject (Stimulation type) *treatment day) was used to assess differences over the treatment trials. Fisher's post hoc test was used to identify group differences. Consistent with an overall extinction effect, the effect of treatment day on freezing is significant $F ((4, 24)=26.662, p<0.001)$. A post hoc analysis revealed a significant treatment effect of exponential stimulation on freezing relative to sham controls (Fisher's PLSD, $p=0.0171$). These findings are consistent with an enhancing effect of vagus nerve stimulation on extinction over repeated treatment trials at about two weeks after conditioning. The error bars are SEM.

The results repeat literature findings in demonstrating that VNS enhances the ability of rats to learn and remember events. The task described below is taken as a fear-conditioning test.

The preliminary results were consistent with reports that VNS enhances memory. Ten Sprague-Dawley rats were implanted with VNS electrodes and stimulated. A single stimulation (0.5 microsecond (ms) biphasic pulses; 20 Hertz (Hz); 30 seconds (s); 0.4 milliampere (mA)) of the vagus nerve in rats immediately after the training trial enhanced memory for a fear conditioning task. These parameters were selected because they enhanced memory in previous reports. We found that VNS-treated rats spent significantly more time avoiding the context where they received a foot-shock at about 48 hours earlier (p-0.017 vs. sham control, n=5/group). These findings suggest that VNS enhances the consolidation of the memory for the association between a context and foot-shock.

Extinction training is a commonly used animal model for Exposure Therapy. As in Exposure Therapy, animals undergoing extinction training learn to make new associations that compete with the old memories.

The next experiment demonstrated that paired VNS increases the rate of extinction of fear memories in rats. This provides proof of concept for enhancing extinction. Extinction training was performed either about one day or about two weeks after induction of the initial fear conditioning. This set of studies provides proof of concept that VNS may enhance extinction long after the initial learned fear event. PTSD may take months to develop and even longer for sufferers to seek treatment. For a treatment to be useful, it must also be effective when initiated long after a trauma. A third experiment examined the duration of the effect of VNS-enhanced fear extinction. Because the spontaneous recovery of fear memories after extinction has been observed in human and non-human animals, it may be important to examine whether the effects of VNS aided extinction training are long lasting.

Each animal was initially anesthetized in an induction chamber filled with isofluorane gas. When the anesthetic took effect, animals were removed from the induction chamber and fitted with a nose cone through which isofluorane mixed with oxygen flows. Animals were shaved at the ventral region of the neck just above the clavicle and from the base of the skull to just ventral to the eyes. Both regions were swabbed with about 70% ethanol, then betadine. An incision was made on the top of the head to expose the skull and two anchor screws were placed lateral of bregma.

Biocompatible micro-renathane tubing (0.04 inch (in.) inner diameter (i.d.), 0.08 in. outer diameter (o.d.), 4 millimeter (mm) long) with a longitudinal slit was used as the electrode cuff.

Two about 7 centimeter (cm) long and about 0.006 in. diameter, TEFLON-insulated, multi-stranded platinum-iridium wires were inserted so that each lead penetrated the cuff lumen and was looped securely around both sides of the slit opening such that the wire within the cuff lumen was uninsulated. Stimulating poles were separated by about 2 mm.

The stimulating cuff was connected to the implant and securely fastened to the skull with dental acrylic. The vagus nerve was accessed at the cervical level through an incision made in the skin along the ventral midline, approximately two cm in length to a depth where the first superficial muscle layers become visible. The muscle layers were separated, exposing the vagus nerve and carotid artery. The stimulating electrode was tunneled subcutaneously to the incision site and placed near the nerve. The nerve was isolated from the connective tissue and placed into the cuff electrode. To insure connectivity of the experimental setup, about 0.2 mA stimulation was administered into the head implant and cessation of breath was assayed.

Twenty rats were implanted with bipolar platinum iridium cuff electrodes around the left vagus nerve. Rats were submitted to auditory fear-conditioning in which a pure tone (about 30 s, about 80 decibel (dB), about 5 kilohertz (kHz)) was paired with a foot shock (about 0.5 mA, about 1 s, co-terminating with tone) over about four trials/day, for about two days, with about three, four, or five min inter-trial interval beginning about three min after being placed in the chamber. About twenty-four hours later, rats were placed in the extinction context again. Under these conditions, when the tone was presented, animals would freeze for a period of time. Percent time spent freezing (time spent freezing/total time in the behavioral apparatus), defined as the absence of all non-respiratory movement, served as the index of fear memory. This test trial was followed by further extinction 24 hours later. Twenty "sham" control rats were implanted with vagal cuff electrodes and were submitted to the same training and extinction protocols described above. Leads from the cuff to the stimulator were attached during training; however, no stimulation was given to this control group. The experimental group was administered VNS (about 0.5 ms biphasic pulses; about 30 s; about 0.4 mA; about 20 Hz, or exponential pulse) applied concurrently with the tone during extinction trials (4 tone exposures/day). A second test trial was given after a single day of extinction. This continued (test, extinction, and test) until VNS-treated rats spent less than 20% of the test time freezing.

Repeated measures ANOVAs were used to compare extinction rate (percent time freezing) across days and a Fisher's post-test were used to identify effects across groups (VNS, sham, un-operated control). All animals showed some extinction to the conditioned stimuli, and the extinction was facilitated in VNS-treated rats compared to both control groups. Significant extinction was reached sooner in VNS-treated than in control rats.

In order to test the effect of VNS paired with extinction training on a second measure of fear conditioning, an attempt to extinguish fear-potentiated startle was made. This task was used by Walker and colleagues to demonstrate D-cycloserine enhancement of extinction in rats and led to the clinical trials of o-cycloserine as an adjunct treatment with exposure therapy in humans suffering from PTSD and phobias. A total of 20 experimental, 20 sham, and 10 un-operated control rats were included in this test of VNS effects on extinction of fear-potentiated startle.

Rats were given about three consecutive days of about 10 min acclimation trials in the experimental chamber. Stable baseline responses were established about 24 hours (hrs) after the acclimation trials. Rats were presented with thirty 95-decibel (dB) startle stimuli with an about 30 s inter-stimulus interval (ISI) for about two consecutive days. These baseline startle stimuli reduced variability in startle responses during test trials.

About twenty-four hours after baseline was established, rats are presented with 10 co-terminating (ISI 3, 4, or 5 min) light (3.7 s) and foot-shock (0.4 mA, 0.5 s) pairings. About twenty-four hours later, a short test was given to establish an initial percent fear-potentiated startle measure (light with startle−startle alone/startle alone×100). The startle response was measured by accelerometer activity transformed into an analog electrical signal and transmitted to a programmable real time processor to measure time over threshold (TOT). About twenty light with startle (3.7 s light, co-terminating 0.5 s startle stimuli) or startle alone (0.5 s startle stimuli) probe trials were presented (30 s ISI) in pseudo-random order.

No probe trial was repeated more than twice. Accelerometer wave data was acquired from a real-time processor and stored for analysis by MATLAB (The Mathworks). About twenty-four hrs later, rats were presented with 30 light (3.7 s) alone extinction exposure trials (ISI 30 s). This extinction trial was followed with vagus nerve stimulation (0.4 mA; 0.5 ms biphasic pulses; 20 Hz, 30 s) delivered by a programmable RX7G-4 stimulator base station and stimulator measuring time over threshold (TOT) and programmed in MATLAB (The Mathworks). About twenty-four hrs after extinction training, rats were presented with 60 light-startle, startle-alone probe trials (ISI 30 s) in pseudo-random order. The effect of VNS on extinction was measured by an ANOVA comparing startle response across the three treatment groups, followed by a Fisher's post-test to identify significant group effects.

A single day of extinction produces a minimal extinction against which the facilitation of treatment can be observed. Therefore, VNS-treated rats were expected to demonstrate greater extinction than sham or un-operated controls. This enhanced extinction may be comparable with the successful dose of o-cycloserine. Additional groups of 20 experimental, 20 sham, and 10 un-operated control rats underwent auditory fear conditioning and extinction, however, the extinction trials were given about two weeks after initial training. VNS implantations in rats remained viable for months. While about two weeks may not seem like sufficient time to wait to begin therapy, it is a significant amount of time relative to the lifespan of a rat (about 2-3 years in the wild) and it is far longer than the more commonly used delay of about 24 hrs. Percent of time spent freezing was quantified for each rat and for each extinction trial.

Repeated measures ANOVAs were used to compare extinction rate (percent time freezing) across days and a Fisher's post-test may be used to identify effects of group (VNS, sham, un-operated control).

Of the two tasks, auditory fear conditioning was preferred because it is a simple task and can be used to address questions about the specificity of extinction to various cues. To determine the duration of the extinction effect, a single retention test was given about two weeks after the last auditory fear conditioning extinction trial. Percent of time spent freezing was quantified for each rat. Mean percent time spent freezing was compared across groups of auditory fear-conditioned rats using an ANOVA with a Fisher's post test to identify significant group effects. Finally, conditioned fear was extinguished about two weeks after rats were trained on auditory fear conditioning. The effect of VNS on extinction were measured by an ANOVA comparing freezing response across three treatment groups (VNS vs. sham controls), followed by a Fisher's post-test.

Although the stimulation parameters proposed were optimized for memory, additional stimulation parameters were investigated, including changes in stimulation intensity (from about zero to about 0.8 mA), duration (about 100 ms to about 30 s) and frequency (about 10 to about 150 Hz) and bandwidth according to parameters optimized for cortical plasticity. Voltage controlled capacitive discharge was tested and was effective. Timing in relationship to the conditioning event and the use of additional and/or longer training times are also variables that may be optimized.

The findings above indicate that exposure therapy can be enhanced by providing an exposure therapy to a patient while simultaneously stimulating the patient's vagus nerve. The nature of the exposure therapy depends on the condition being treated. For example, for post-traumatic stress disorder, the therapy event may be a sensory recreation of the traumatic event, presented in a controlled environment. The precise timing of the paired VNS pulse depends on the nature of the therapy event. The results indicate that the paired VNS pulse may be given during the therapy rather than before or after, although some overlap is not contraindicated. Where a trigger event can be identified in the therapy event, such as a tone or flash, the pairing can be derived from the trigger event. Exposure therapy of this kind can be used to treat post-traumatic stress disorder, phobic disorders, obsessive-compulsive disorder, addiction disorders including addiction relapse, and other memory extinction disorders. VNS can be paired effectively with any of these known therapies.

None of the description in the present application should be read as implying that any particular element, step, or function is an essential element that must be included in the claim scope: the scope of patented subject matter is defined only by the allowed claims. Moreover, none of these claims is intended to invoke paragraph six of 35 U.S.C. section 112 unless the exact words "means for" are followed by a participle. The claims as filed are intended to be as comprehensive as possible, and no subject matter is intentionally relinquished, dedicated, or abandoned.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 5, 4, etc.; greater than 0.10 includes 0.11, 0.12, 0.15, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 5 percent, 4 percent, 5 percent, . . . , 50 percent, 51 percent, 52 percent, . . . , 75 percent, 76 percent, 77 percent, 78 percent, 77 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

The invention claimed is:

1. A post-traumatic stress disorder (PTSD) therapy method comprising:
   providing, to a patient, an exposure event which is sensory-recreative of a traumatic event that contributed to the PTSD; and
   electrically stimulating the patient's vagus nerve during the exposure event.

2. The method of claim 1, wherein said therapy is a memory extinction therapy.

3. The method of claim 1, wherein said patient's vagus nerve is stimulated using a voltage controlled capacitive discharge stimulation pulse.

4. The method of claim 1, wherein said patient's vagus nerve is stimulated electrically with a stimulation intensity less than about 0.8 mA or about 0.8 mA.

5. The method of claim 1, wherein said therapy is an addiction therapy.

6. The post-traumatic stress disorder therapy method of claim 1, wherein said exposure event contains sensory recreations of a traumatic event.

7. The post-traumatic stress disorder therapy method of claim 1, wherein said patient's vagus nerve is invasively stimulated electrically.

8. The method of claim 7, wherein the action of providing the exposure event to the patient and the action of stimulating the patient's vagus nerve during the exposure event results in a reduction of the post-traumatic stress disorder of the patient.

9. The method of claim 1, wherein the patient is a patient where the PTSD took months to develop following an initial exposure to a traumatic event that resulted in the PTSD.

10. The method of claim 1, wherein the actions of providing exposure events and stimulating the patient's vagus nerve occur long after a traumatic event that resulted in the PTSD.

11. The method of claim 1, wherein the actions of providing exposure events and stimulating the patient's vagus nerve are part of an extinction training regime, wherein the extinction training regime is commenced two weeks after induction of an initial fear conditioning.

12. The post-traumatic stress disorder therapy method of claim 11, wherein said patient's vagus nerve is stimulated invasively utilizing an electrical current from a device.

13. The method of claim 1, wherein the actions of providing exposure events and stimulating the patient's vagus nerve facilitate a natural extinction process of the patient that protects most people from developing post-traumatic stress disorder.

14. The method of claim 1, wherein said therapy is a memory extinction therapy, the memory extinction therapy alleviating, at least in part, the post-traumatic stress disorder.

15. A phobia disorder therapy method comprising:
    providing, to a patient, an extinction event which is sensory-recreative of something that contributed to the phobia; and
    electrically stimulating the patient's vagus nerve during the extinction event, thereby at least partially alleviating the phobia disorder.

16. The method of claim 15, further comprising:
    executing a retention test to determine a duration of an extinction of the phobia.

17. The phobia disorder therapy method of claim 15, wherein said patient's vagus nerve is invasively stimulated electrically.

18. The method of claim 17, wherein said patient's vagus nerve is stimulated using a constant current stimulation pulse.

19. The method of claim 17, wherein said patient's vagus nerve is stimulated using a voltage controlled capacitive discharge stimulation pulse.

20. The method of claim 17 wherein a stimulation intensity is less than about 0.8 mA or about 0.8 mA.

21. The method of claim 17, wherein a duration of the stimulation is about 100 ms to about 30 s.

22. The method of claim 17, wherein a frequency of the stimulation is about 10 to about 150 Hz.

23. The method of claim 17, wherein the action of providing the extinction event to the patient and the action of stimulating the patient's vagus nerve during the exposure event results in a reduction of the phobia disorder of the patient.

24. An obsessive-compulsive disorder (OCD) therapy method comprising:
    providing, to a patient, a therapy event which is sensory-recreative of something that contributed to the OCD; and
    electrically stimulating the patient's vagus nerve during the therapy event.

25. The obsessive-compulsive disorder therapy method of claim 24, wherein the action of providing the therapy event entails providing an exposure event to the patient.

26. The method of claim 25, wherein the action of providing the therapy event to the patient and the action of stimulating the patient's vagus nerve during the exposure event results in a reduction of obsessive-compulsive disorder.

27. The method of claim 24, wherein said patient's vagus nerve is stimulated utilizing an electrical current from a device.

28. An addiction disorder therapy method comprising:
providing, to a patient, a therapy event which is sensory-recreative of something that contributed to addiction-disorder; and
electrically stimulating the patient's vagus nerve during the therapy event.

29. The addiction disorder therapy method of claim 28, wherein the action of providing the therapy event entails providing an exposure event to the patient.

30. The method of claim 29, wherein the action of providing the therapy event to the patient and the action of stimulating the patient's vagus nerve during the exposure event results in a reduction of the addiction disorder.

* * * * *